United States Patent [19]

Jeffreys

[11] Patent Number: 5,263,486
[45] Date of Patent: Nov. 23, 1993

[54] APPARATUS AND METHOD FOR ELECTROCARDIOGRAM DATA COMPRESSION

[75] Inventor: Anthony M. Jeffreys, Elanora Heights, Australia

[73] Assignee: Telectronics Pacing Systems, Inc., Englewood, Colo.

[21] Appl. No.: 876,065

[22] Filed: Apr. 28, 1992

[30] Foreign Application Priority Data

Nov. 1, 1991 [AU] Australia .............. PK 9244

[51] Int. Cl.$^5$ .............................................. A61B 5/04
[52] U.S. Cl. ................... 128/696; 128/703; 128/704; 128/708; 364/413.06
[58] Field of Search ............... 128/696, 700, 702, 703, 128/704, 706, 708; 364/413.06

[56] References Cited

U.S. PATENT DOCUMENTS

| | | | |
|---|---|---|---|
| 4,499,548 | 2/1985 | Beebe | 364/575 |
| 4,503,510 | 3/1985 | Weaver | 364/715 |
| 4,633,884 | 1/1987 | Imai et al. | 128/696 |
| 4,862,897 | 9/1989 | Eisenberg et al. | 128/696 |
| 4,882,754 | 11/1989 | Weaver et al. | 128/696 |
| 4,920,489 | 4/1990 | Hubelbank et al. | 364/413.06 |
| 4,947,858 | 8/1990 | Smith | 128/708 |

FOREIGN PATENT DOCUMENTS 3827808 5/1989 Fed. Rep. of Germany .

OTHER PUBLICATIONS

Computers in Cardiology, *IEEE*, Sep. 25, 1988, pp. 569–572, Washington, D.C., N. C. Smith et al., "An ECG Compression Algorithm for Full Disclosure in a Solid-State Real-time Holter Monitor".

*Primary Examiner*—William E. Kamm
*Assistant Examiner*—George Manuel
*Attorney, Agent, or Firm*—Gottlieb, Rackman & Reisman

[57] ABSTRACT

An improved electrocardiac monitoring device is disclosed in which the sampling period utilized to sample the ECG signal is varied dynamically. Specifically, during rapidly varying portions of the ECG signal, the sampling rate is high. As the rate of change of the ECG signal decreases, the sampling rate is slowed so that only the minimum number of samples are taken to accurately reconstruct the analog ECG signal. The sampling period to be used is determined from the relative positions in time between a predetermined portion of the ECG signal and the portion of the ECG signal being sampled.

10 Claims, 2 Drawing Sheets

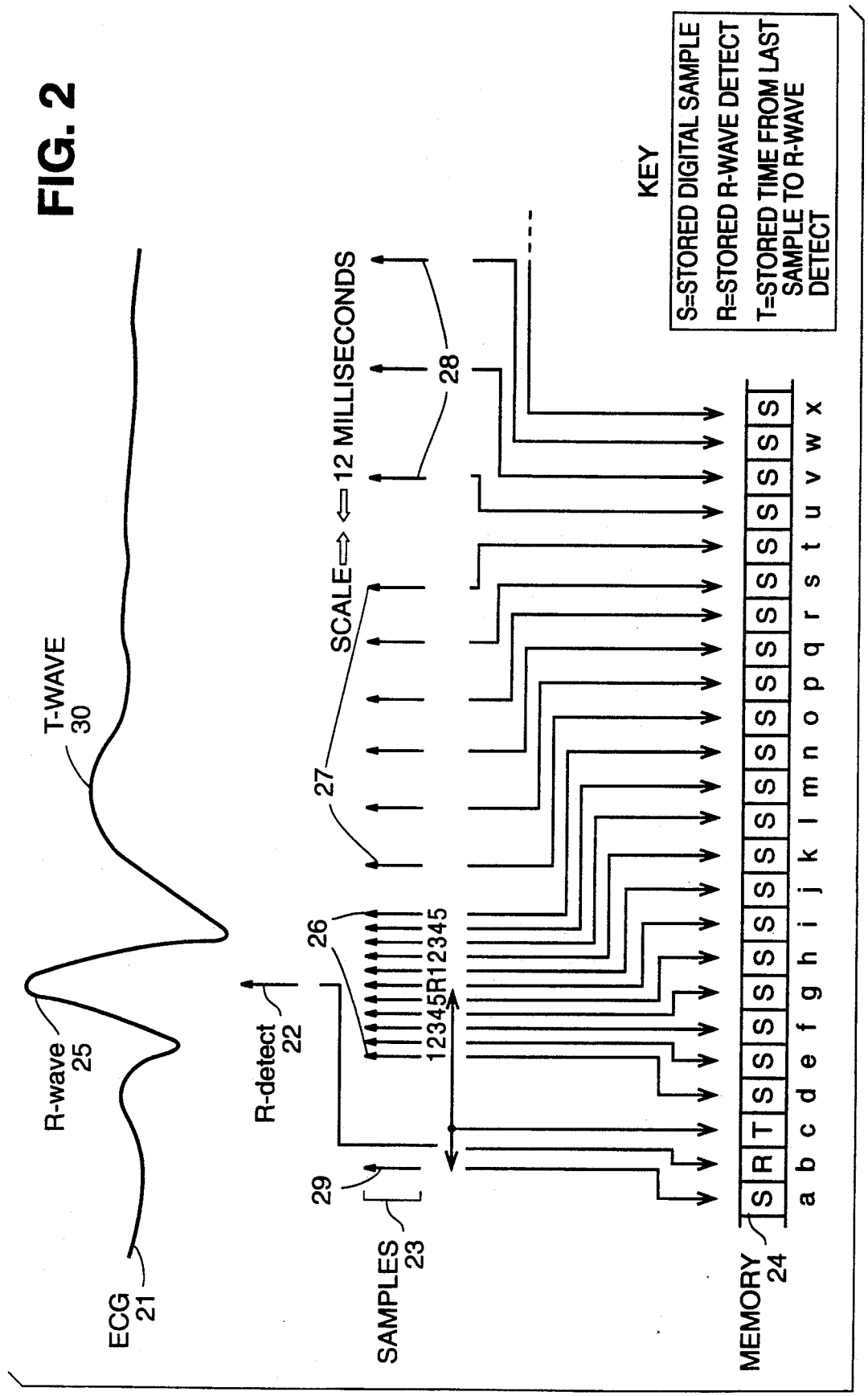

APPARATUS AND METHOD FOR ELECTROCARDIOGRAM DATA COMPRESSION

BACKGROUND OF THE INVENTION

This invention relates to an improved signal storage and processing system for compressing and reproducing electrocardiogram (ECG) signals.

DESCRIPTION OF THE PRIOR ART

Recent advances in implantable pacemakers/defibrillators and Holter monitors allow for digital storage and processing of ECG signals. Typically, an analog ECG signal is sampled and a plurality of digital samples are stored in an internal memory device. The stored samples can be retrieved later and the analog ECG signal can be reconstructed therefrom. Thus, the physician can program the device to sample the ECG output from the heart during certain times and store the samples for later analysis of the ECG signal by the physician.

It is advantageous to minimize the number of samples of data required to be stored in order to reconstruct the analog ECG signal. One reason is that each time the analog signal is sampled and the sample stored, power is consumed, thereby shortening battery life. Furthermore, many prior art ECG analysis techniques require power consuming digital signal processing algorithms. As the number of samples increases, so does the power consumption of the signal processing algorithm. Finally, since the samples must be stored in memory for later analysis and/or reconstruction of the analog ECG signal, minimizing the number of stored samples minimizes the amount of memory required.

U.S. Pat. No. 4,503,510 to Weaver is directed to a method and apparatus for digital data compression. Compression of the data represents one possible solution to the above problem. Digital signals to be stored are first compressed using a finite-impulse response digital compression filter which generates estimated signal values which are then subtracted from actual signal values to provide a sequence of difference signals. The difference signals are then encoded using a Huffman type encoding technique in order to minimize the number of bits required to store the information. The Weaver arrangement, when compared to a conventional pulse code modulation sampling system, significantly reduces the number of bits of information which must be stored to reconstruct and/or process the ECG signal.

U.S. Pat. No. 4,499,548 to Beebe describes a data compression apparatus which selects for display a data sample of each non-overlapping and successive group of data samples which differs the most in amplitude from the average amplitude of the previous group of data samples, and also selects and displays the data sample of each group which differs the most in amplitude from the data sample selected for display from the previous group. The arrangement of Beebe also significantly reduces the number of data samples which must be stored to reconstruct an analog ECG signal.

U.S. Pat. No. 4,633,884 to Imai, et al., discloses a digital processing system utilizing several digital filters to minimize the number of samples being stored.

All of the known prior systems require extensive data processing in order to compress the data to be stored. Thus, in an attempt to minimize the number of samples to be later processed in reconstructing the ECG signal, the ECG samples must be extensively processed before they are stored in the first place. Accordingly, the prior art techniques are, in some sense, self-defeating.

SUMMARY OF THE INVENTION

The above and other problems of the prior art are overcome in accordance with the present invention which relates to a novel digital signal storage and processing technique for storing a digital representation of an ECG signal and for reconstructing the ECG signal at a later time. The present invention utilizes the fact that the ECG signal varies rapidly during certain portions thereof and varies quite slowly during other portions. Moreover, there is a large part of the ECG signal which is nearly constant over a long period of time.

The present invention utilizes multiple sampling rates which sample the signal at low, medium and high sampling rates, depending upon whether the signal is not varying, varying slowly, or varying rapidly, respectively. The determination of how fast the signal is varying is based upon the relative positions, in time, between the portion being sampled and the R-wave. Unlike conventional variable rate sampling systems, the sampling rate is not determined by continuously calculating estimates of the derivative of the analog signal being sampled. Rather, the derivative, and thus the required sampling rate, are assumed from the relative time positions of the R-wave and the portion of the signal being sampled. Thus, the complex power consuming operation of constantly estimating a derivative is unnecessary.

The arrangement ensures that the sampling rate is always great enough to reconstruct the signal, but that the sampling rate is never faster than it needs to be during slowly varying portions of the ECG signal being sampled. Thus, the number of required samples is minimized. It should also be noted that other encoding techniques may be further utilized to minimize the number of stored samples even more.

BRIEF DESCRIPTION OF THE DRAWINGS

FIG. 2 shows an exemplary ECG signal and a digital representation of the ECG signal which is stored in accordance with the techniques of the present invention.

DETAILED DESCRIPTION OF THE PREFERRED EMBODIMENT

Figure 1:
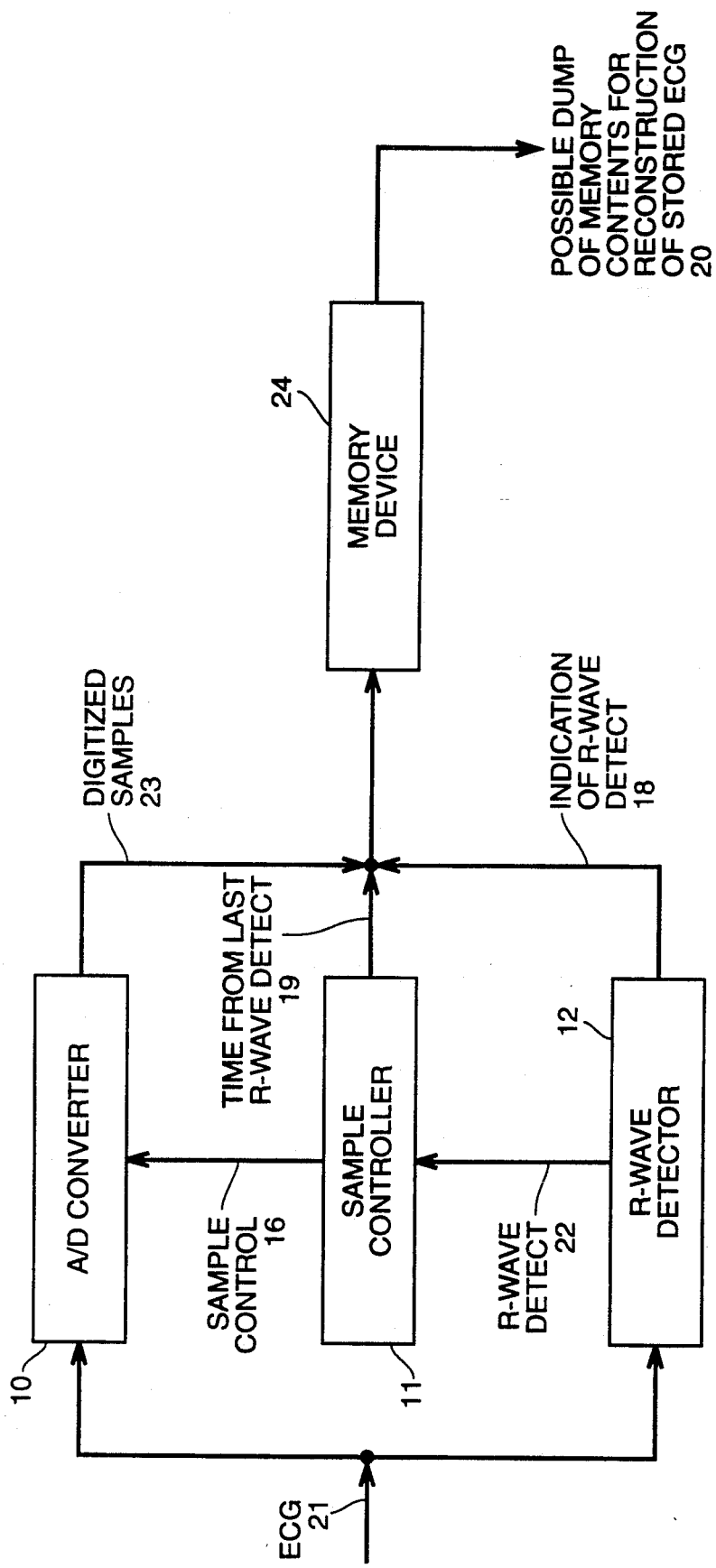
FIG. 1 depicts in block diagram form the major components to be installed in an implantable pacemaker/-defibrillator for implementation of the present invention.

FIG. 1 shows the basic components of an exemplary system for implementation of the present invention, an analog to digital converter (A/D) 70, a sample controller 11, an R-wave detector 12 and a memory device 24. As is well known in the art, A/D converter 10 must sample the incoming ECG signal 21 at a minimum rate as required by the well-known Nyquist sampling theory. The Nyquist rate is proportional to the rate at which the incoming ECG signal varies, i.e., the first order derivative. The faster the incoming ECG signal varies, the more frequently it must be sampled in order to ensure accurate reconstruction.

The R-Wave detector transmits an R-Wave detect 22 to sample controller 11. The sample controller 11 controls A/D converter 10 via a sample control signal 16. The digitized samples 23 and an R-Wave detect signal 18, as well as a time signal 19 which indicates the time from the last R-wave detect, are all transmitted to memory device 24 as indicated.

In operation, R-wave detector 12 monitors the incoming ECG signal for the presence of R-waves. Once R-wave detection occurs, sampling and A/D conversion for the associated cardiac cycle begins. The sampling interval is adjusted at predetermined times after R-wave detection since the rate of change of the ECG signal slows considerably at predetermined times after the R-wave is detected. An exemplary system with the preferred sample rate is described below with reference to FIG. 2.

FIG. 2 shows an ECG signal 21 including an R-wave 25 and a T-wave 30. Shown in conceptual form beneath the R-wave are ECG samples 23. The samples are arranged into 4 groups 26-29, each of which is taken at a different sampling rate. Memory 24 is also shown in FIG. 2 in conceptual form for purposes of explaining the types and quantities of information which must be stored therein for accurately reconstructing the ECG signal.

In operation, an R-wave 25 is detected and R-wave detector 12 generates the R-wave detect 22 signal. R-wave detect 22 is input into sample controller 11 which causes sample controller 11 to generate samples at 12 ms. intervals. FIG. 2 shows five such samples immediately prior to the R-wave detect. These first five samples require an analog delay line or any other system capable of storing the ECG prior to the R-wave (e.g., an additional digital register arranged to store past samples) so that when the R-wave is detected, the analog signal just prior to the R-wave detect will still be available. As shown in FIG. 2, five additional closely spaced samples, immediately subsequent to the R-wave detect, are then taken for a total of ten closely spaced samples 26.

Following the ten samples at 12 ms. intervals, the sampling interval is increased to 48 ms. FIG. 2 shows six samples 27 spaced 48 ms. apart from one another. Thereafter, three samples 28 are taken at 96 ms. intervals. Thereafter, all samples have a period of 192 ms. until the last sample of group 29, just prior to the next R-wave detect. It can be appreciated from comparing ECG signal 21 to the samples 23 shown below it that during the flat portion of the ECG signal 21 following T-wave 30, samples are taken at large intervals, while during the rapidly varying portions surrounding R-wave 25, samples are taken much more frequently.

The sampling rules ensure that the ECG signal is sampled at a fixed and nominally short interval (12 ms.) around the R-wave detect point 22, and that the sample period is increased to 48 ms., then to 96 ms., and finally to 192 ms. as the required Nyquist rate for the ECG signal being sampled decreases. The sequence of sampling periods for an ECG cycle is denoted herein as a "sample profile."

Since the stored samples will be used to reconstruct an analog ECG signal, memory 24 must not only store the values of the samples themselves, but must store information sufficient to permit the reconstruction algorithm and/or hardware to determine the proper sampling interval and the time of R-wave detect 22. As show in FIG. 2, memory 24 stores not only the values of the individual digital samples of the ECG signal, but also stores the R-wave detects. Additionally, a value T is stored after each R-wave detect (22), where T indicates the amount of time between the last sample (taken after a 192 ms. interval in the example herein) and the R-wave detect itself.

The stored information from memory 24 may be utilized to reconstruct the analog ECG signal. The stored information is read from memory 24 via electrical path 20, as shown in FIG. 1. Specifically, with reference to memory 24 of FIG. 2, the individual memory locations have been labeled a-x. As can be seen from FIG. 2, the time T stored in location c, coupled with the R-wave detect from location b and the ten samples, d through m, can be used to reconstruct the analog ECG signal which immediately surrounds the R-wave detect 22. The remaining samples are at known sampling intervals and are simply utilized by a conventional D/A converter to reconstruct the ECG signal. The D/A converter may be programmed to specifically implement the technique.

The purpose of storing the time T is that the sampling interval between any two successive samples is known for the entire ECG signal, except for the sampling interval between the last sample of the group of samples 29 and the first sample of the group of samples 26. The time T allows this one unknown sampling interval to be determined by the reconstruction algorithm/hardware. Once T is known, reconstruction of the analog ECG signal may be done utilizing conventional components in a straightforward manner which will not be described in detail herein. The number of samples at the slowest rate varies from cycle to cycle, but recognition of R in effect determines the last sample stored for a cycle.

The above describes the preferred embodiment and sampling intervals, although it is obvious that other variations and sample profiles will be apparent to those of ordinary skill in the art. For example, while the embodiment described herein utilizes a ventricular ECG signal, an atrial ECG signal may also be monitored and stored in a similar manner. An atrial ECG signal would require replacing the R-wave detector described herein with a P-wave detector. Indeed, any portion of the ECG signal may be detected, and the derivative and required sampling rate assumed from the relative time positions of the portion of the signal being sampled and that detected.

It is contemplated that the sample profile may be varied at the physician's discretion, and may even be programmable by telemetric means which are well known in the art and are in wide-spread use for varying pacemaker/defibrillator parameters in known pacemaker systems.

I claim:

1. Apparatus for providing a digital representation of an electrocardiac (ECG) signal, said apparatus comprising:

means for detecting a predetermined portion of said ECG signal;

means for sampling a ECG signal to generate a plurality of digital samples which correspond proportionally to the amplitude of said ECG signal and are separated from one another by sampling intervals, said sampling intervals being adjustable; and means responsive to said detecting means for adjusting the sampling intervals, based upon time differences between said predetermined portion and respective portions of said ECG signal being sampled, whereby the digital samples include samples generated at more than one interval.

2. Apparatus according to claim 1 further comprising means for storing said digital samples.

3. Apparatus according to claim 2 further comprising means for storing additional information sufficient to determine the sampling intervals at which all of the digital samples were sampled.

4. Apparatus according to claim 1 wherein said means for detecting is an R-wave detector.

5. Apparatus according to claim 1 wherein said means for detecting is a P-wave detector.

6. A method of providing a digital representation of an electrocardiac (ECG) signal, said method comprising the steps of:

detecting a predetermined portion of said ECG signal;

sampling the ECG signal to generate a plurality of digital samples which correspond proportionally to the amplitude of said ECG signal and are separated from one another by sampling intervals, said sampling intervals being adjustable; and adjusting the sampling intervals in response to said detecting step, said step of adjusting being based upon time differences between said predetermined portion and respective portions of said ECG being sampled, whereby the digital samples include samples generated at more than one interval.

7. The method according to claim 6 further comprising the step of storing said digital samples.

8. The method according to claim 7 further comprising the step of storing additional information sufficient to determine the sampling intervals at which all of the digital samples were sampled.

9. The method according to claim 6 wherein said step of detecting includes the sub-step of detecting an R-wave.

10. The method according to claim 6 wherein said step of detecting includes the sub-step of detecting a P-wave.

* * * * *